United States Patent
Franke et al.

(10) Patent No.: US 7,636,457 B2
(45) Date of Patent: Dec. 22, 2009

(54) SYSTEMS AND METHODS FOR ASSESSING DISORDERS AFFECTING FINE MOTOR SKILLS USING HANDWRITING RECOGNITION

(75) Inventors: William E. Franke, McLean, VA (US); Mark Walch, Lake Ridge, VA (US)

(73) Assignee: Gannon Technologies Group LLC, McLean, VA (US)

( * ) Notice: Subject to any disclaimer, the term of this patent is extended or adjusted under 35 U.S.C. 154(b) by 807 days.

(21) Appl. No.: 10/896,642

(22) Filed: Jul. 21, 2004

(65) Prior Publication Data
US 2005/0053269 A1    Mar. 10, 2005

Related U.S. Application Data

(60) Provisional application No. 60/489,074, filed on Jul. 21, 2003.

(51) Int. Cl.
*G06K 9/00* (2006.01)
(52) U.S. Cl. .............. 382/119; 382/128; 600/300; 600/595; 128/922; 128/923
(58) Field of Classification Search ............... 382/182, 382/186–188, 181, 119
See application file for complete search history.

(56) References Cited

U.S. PATENT DOCUMENTS

| | | | | |
|---|---|---|---|---|
| 3,588,822 A | * | 6/1971 | Yamamoto | 382/202 |
| 4,885,687 A | * | 12/1989 | Carey | 434/261 |
| 4,922,925 A | * | 5/1990 | Crandall et al. | 600/595 |
| 4,961,231 A | | 10/1990 | Nakayama et al. | |
| 5,559,895 A | * | 9/1996 | Lee et al. | 382/119 |
| 5,562,104 A | | 10/1996 | Hochberg | |
| 5,719,959 A | * | 2/1998 | Krtolica | 382/209 |
| 5,745,600 A | * | 4/1998 | Chen et al. | 382/218 |
| 5,772,611 A | * | 6/1998 | Hocherman | 600/595 |
| 5,854,853 A | | 12/1998 | Wang | |
| 5,854,855 A | | 12/1998 | Errico et al. | |
| 5,885,231 A | * | 3/1999 | Cramer et al. | 600/595 |
| 5,923,793 A | * | 7/1999 | Ikebata | 382/311 |
| 5,930,380 A | * | 7/1999 | Kashi et al. | 382/119 |
| 6,011,537 A | | 1/2000 | Slotznick | |

(Continued)

OTHER PUBLICATIONS

Slavin MJ, Phillips JG, Bradshaw JL, Hall KA, Presnell I. "Consistency of handwriting movements in dementia of the Alzheimer's type: a comparison with Huntington's and Parkinson'diseases". J Int Neuropsychol Soc Jan. 1999;5(1):20-25.*

(Continued)

*Primary Examiner*—Sath V Perungavoor
(74) *Attorney, Agent, or Firm*—Procopio Cory Hargreaves & Savitch LLP; Noel C. Gillespie (57) ABSTRACT

A detection and tracking method that enables an objective determination of changes in handwriting with the passage of time and progress of medical conditions which affect fine motor skills. Specifically, a detection and tracking method which precisely describes a handwriting sample as a plurality of features which become indicators of a medical disorder affecting fine motor skills. The indicators are obtained and characterized using analytical and statistical techniques resulting in the development of diagnostic tools for detection and management of that disorder.

44 Claims, 3 Drawing Sheets

U.S. PATENT DOCUMENTS

| | | | |
|---|---|---|---|
| 6,108,444 | A | 8/2000 | Syeda-Mahmood |
| 6,445,820 | B1 | 9/2002 | Love |
| 6,454,706 | B1 * | 9/2002 | Pullman ............... 600/300 |
| 6,628,847 | B1 * | 9/2003 | Kasabach et al. .......... 382/314 |
| 2002/0035486 | A1 * | 3/2002 | Huyn et al. ............... 705/3 |
| 2005/0053269 | A1 * | 3/2005 | Franke et al. ............. 382/128 |
| 2005/0163377 | A1 * | 7/2005 | Walch ..................... 382/187 |
| 2006/0034516 | A1 * | 2/2006 | Hullender et al. .......... 382/186 |
| 2006/0122472 | A1 * | 6/2006 | Pullman ................... 600/300 |

OTHER PUBLICATIONS

Bain, PG, Findley, LJ, "Standards in Neurology, Series A: Assessment, diagnosis and evaluation, Book I: Assessing Tremor Severity," published by Smith Gordon and Co., Ltd., London, England/ Nishimura Co., Ltd., Niigata-Shi, Japan. (Table of Contents and pp. 1-27), 1993.*

Dehghan, M. "Signature Verification Using Shape Descriptors and Multiple Neutral Networks", IEEE Tencon 96 ,02, Dec. 1997, vol. 1, pp. 415-418.

International Search Report for PCT/US04/29091.

Hilton, et al: "Influence of age and illness on handwriting: Identification problems" Forensic Science, Elsevier, vol. 9, Jan. 1, 1977, pp. 161-172, XP023082329, ISSN: 0300-9432 [retrieved Jan. 1, 1977].

Cobbah W.G.K, et al: "Computer analysis of 1-23 handwriting dynamics during dopamimetic tests in Parkinson's disease" Euromicro Conference, 2000. Proceedings of the 26th Sep. 5-7, 2000, Los Alamitos, CA, USA, IEEE Comput. Soc, US, vol. 2, Sep. 5, 2000, pp. 414-418, XP010514273 ISBN: 978-0-7695-0780-4.

Supplementary European Search Report for EP04778942.5—2218 / 1661059 PCT/US2004/023651 mailed Nov. 28, 2008.

* cited by examiner

SYSTEMS AND METHODS FOR ASSESSING DISORDERS AFFECTING FINE MOTOR SKILLS USING HANDWRITING RECOGNITION

RELATED APPLICATIONS INFORMATION

This application claims priority under 35 U.S.C. §119 to U.S. Provisional Patent Application Ser. No. 60/489,074, entitled "Systems and Methods for Detecting a Neurological Disease Using Handwriting Recognition," filed Jul. 21, 2003, which is incorporated herein by reference in its entirety as if set forth in full. This application is also related to U.S. patent application Ser. No. 10/791,375, entitled "Systems and Methods for Source Language Pattern Matching," filed Mar. 1, 2004, which is also incorporated herein by reference in its entirety as if set forth in full.

BACKGROUND

1. Field of the Invention

The field of the invention relates generally to medical diagnostic tools and more particularly to the use of comparative handwriting analysis in the assessment of conditions which affect fine motor skills such as neurological disorders.

2. Background Information

In providing medical care, the ability to diagnosis and monitor characteristic features of a condition is crucial to the management of that condition. For example, early diagnosis of Parkinson's disease can lead to early therapeutic intervention, the effectiveness of which requires continual monitoring and assessment. Often the diagnosis of a neurological disorder, for example, only occurs awhile after the initial onset of the disease, because the outward manifestations of the disease may begin subtly and progress only slowly over time. Affected individuals may be oblivious to gradually progressive changes in neurological functioning while early detection and intervention may delay or prevent the worsening of functions or of the underlying disorder. Additionally, even after detection, continuous monitoring is generally needed in order to assess the effectiveness of interventions and the progress of the underlying disease.

For conditions which affect fine motor skills such as neurological diseases and myopathic disease, changes in handwriting frequently are observed. For instance, with the onset of aging or a neurological disorder, the handwriting of a subject alters and in general deteriorates. Properly correlated to known benchmarks, handwriting can be used as an indicator of the onset of neurological disorders or non-neurological disorders which affect fine motor skills, and can be used to track progress of these disorders. For example, it has been observed that with the onset of Alzheimer's disease, there is increased frequency in the lifting, wavering, or constriction of pen-stroke. Similarly, it has been noted that early symptoms of Parkinson's disease can include rigidity and resistance to movement. Such symptoms however slight can manifest themselves in handwriting. In fact, the so-called "pill rolling" movement associated with Parkinson's can result in distinctive handwriting features that can be used as an early indicator to the onset of Parkinson's disease. Though early indications of this sort may be indiscernible by human analysis, such indicators can be detected through, for example, the use of computer enhancement and computer handwriting analysis.

Since these types of disorders are often progressive, by noting trends in the changes in certain features of handwriting over a long period of time, early detection of the onset of these types of conditions and the clinical progression of these conditions can be achieved. Features in handwriting such as character topology, dimensions, spacing, proportions and ratios, skew, stroke curvature, line continuity, to name just a few, can be objectively quantified and described. Using analytical and statistical techniques, handwriting features from an individual can then be compared to specific handwriting features known to be indicators of a disorder affecting fine motor skill. This information can be used as a diagnostic assessment tool in the detection and management of that disorder.

Unfortunately, matching handwriting features and quantifying the differences between matched features is conventionally a very time consuming and laborious activity involving highly skilled technicians reviewing samples under microscopes.

SUMMARY OF THE INVENTION

A detection and tracking method that enables an objective determination of changes in handwriting with the passage of time and progress of medical conditions which affect fine motor skills. Specifically, a detection and tracking method which precisely describes a handwriting sample as a plurality of features which become indicators of a medical disorder affecting fine motor skills. The indicators are obtained and characterized using analytical and statistical techniques resulting in the development of diagnostic tools for detection and management of that disorder.

In one embodiment, handwriting samples are transformed by computer software into mathematical graphs consisting of edges and vertices that represent specifications of the handwriting such as letter form topology and proportions, relationship among the sample's internal features, sequence of pen strokes, and strength of these strokes. The graphs are analyzed to determine those relevant indicators which are attributable to a given relevant disorder and to determine how those indicators change over time and progression of that disorder. The results of this analysis can then be used to compare handwriting samples from other individuals as a means to detect the onset of new disease or to monitor the development of known disease.

These and other features, aspects, and embodiments of the invention are described below in the section entitled "Detailed Description of the Preferred Embodiment."

BRIEF DESCRIPTION OF THE DRAWINGS

Features, aspects, and embodiments of the inventions are described in conjunction with the attached drawings, in which.

DETAILED DESCRIPTION OF THE PREFERRED EMBODIMENT

The systems and methods below disclose a computer based system for performing the analysis facilitates the development and application of handwriting feature indicators. These indicators are then used in a medical diagnostic tools in the assessment of conditions affecting fine motor skills such as neurological disorders, myopathic disorders, or even non-disease changes associated with the normal aging process. The descriptions below should not, however, be seen as, limiting the invention to any particular computer system or set of algorithms for detecting changes associated with the aging process, unless otherwise indicated.

In the systems and methods described below, differences and similarities between handwriting samples can be correlated with the onset or progression of medical disorders that affect fine motor skills such as neurological disorders or non-neurological disorders like myositis and myopathy (collectively the "target disorders"), as well as changes associated with the normal aging process. Such a system can involve a precise comparative analysis of handwriting and can permit an automated determination of whether changes in handwriting with the passage of time are attributable to a target disorder. By identifying and following features of handwriting samples that are attributable to a disorder, a system configured as described below can provide a means to determine the correlation of those features and the onset of the disorder, the pace and course of the disorder, and a means for the objective measurement of the effectiveness of therapeutic interventions.

Figure 1:
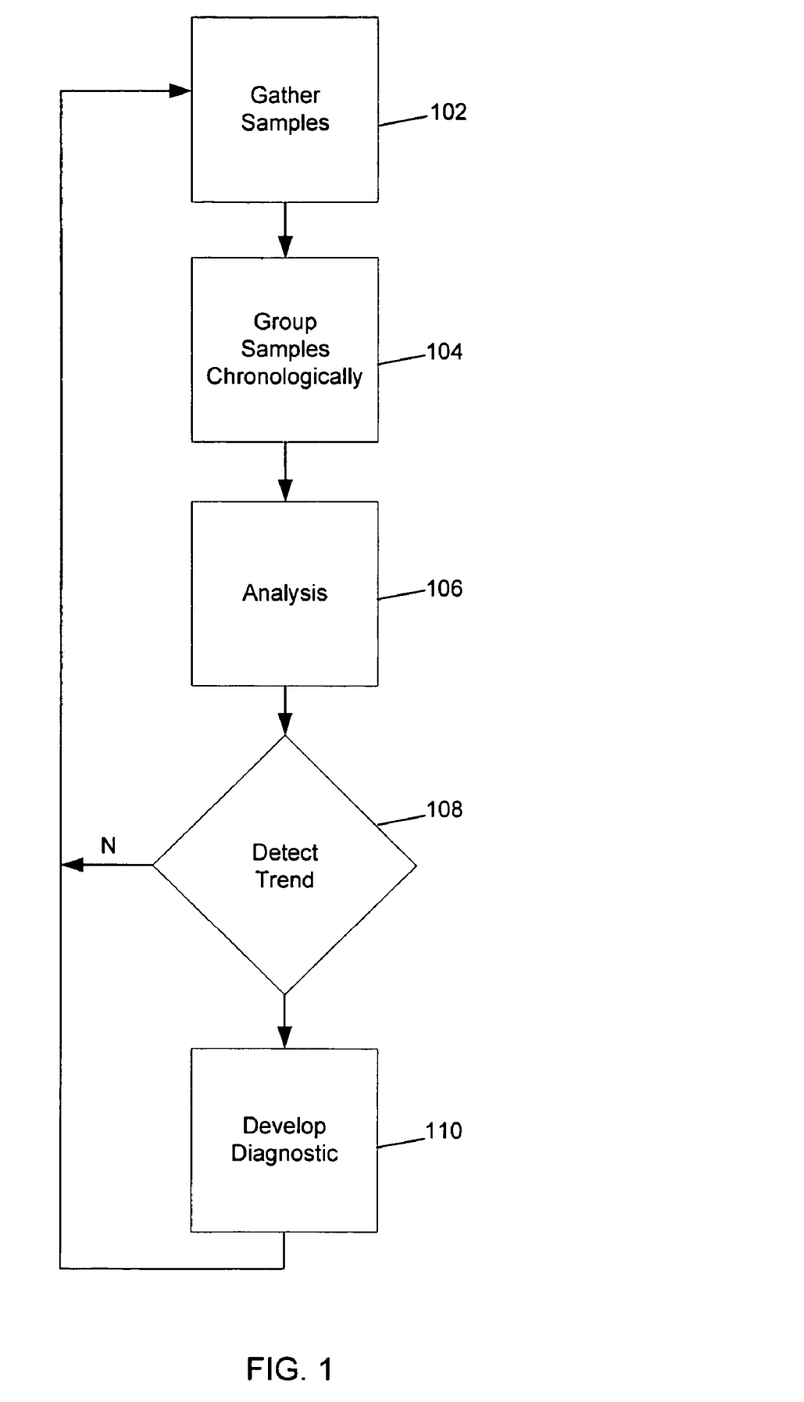
FIG. 1 is a flow chart illustrating an example methodology for detecting target disorders in accordance with one embodiment.

Thus, a set of diagnostic criteria and tools can be developed from the analysis of handwriting in accordance with the systems and methods described herein. FIG. 1 is a flow chart illustrating one example embodiment of a methodology for developing a set of diagnostic criteria. First, in step 102, a set of indicators of a neurological disorder can be developed using handwriting analysis. In developing such indicators, handwriting samples from a variety of subjects known to be afflicted with a given neurological disorder can be gathered spanning a period of years. The span of samples can vary based on the disorder being analyzed. A more rapidly degenerative disorder can, for example, require a shorter span than a slower degenerative disorder. The qualities and requirements of the sample set is described further below.

Next, in step 104, the analysis of handwriting samples can be chronologically grouped into sets that cover three-month quarters. The first step in the process can be to establish the chronological boundaries of the participant's sample base. The samples can then be quantified and averaged. Depending on the implementation, extreme anomalies can be dismissed so that they do not unduly affect the process. The average of each feature can then be charted against time. For example, the average character size for a give handwriting character can be charted against time over the analysis period and compared against the character size at the inception of the test.

Next, in step 106, expert analysis using analytical and statistical techniques of various features for each subject in the group is undertaken to determine if a trends in feature changes can be attributed to the neurological disorder. When a trend is detected, in step 108, then it can be used to develop diagnostic tools, in step 110, to use handwriting as an indicator of the onset of the neurological disorder. It should be noted that such trends should have some distinguishing characteristics from other neurological disorders.

This process can be applied, for example, to the development of objective analytical tools for Alzheimer's disease, Parkinson's disease, front to temporal dementia, dementia with Lewy bodies, and Huntington's disease, to name just a few.

Feature analysis can be accomplished, for example, using the systems and methods described in related application Ser. No. 10/791,375, which is incorporated herein by reference. In this related applications, systems and method are disclosed for reducing handwriting samples to a set of graphs that can then be compared, using pattern matching techniques. The technology disclosed in application Ser. No. 10/791,375 is briefly summarized below.

In one embodiment, features to be analyzed in the above process can be categorized into two classes, dynamic and static features. Dynamic features indicate occurrences in the activity of writing, such as pen-pressure or line-integrity. Static features encompass those features that are attributes of the manner characters, groups of characters and parts of characters are formed, such as character topology and proportions.

Thus, dynamic features can be used in determining the onset of neurological disorders. For example, the alternating burst of strength and loss of control in early stage Parkinson's disease can manifest itself in pen pressure inconsistency. Furthermore, the speed of writing can be indicative of writing confidence, which would be lower in a subject with a neurological disorder. The breakdown of line continuity within words and between words can also increase with the onset of neurological disorders. Deterioration of the steadiness of writing can also indicate a neurological disorder. The connectivity of characters can also serve as an indicator of a neurological disorder. For example, the existence and number of disconnected isolated random stroke can indicate difficulty commencing writing or recalling the constructive sequence for writing. Depending on the embodiment, all or some of the above dynamic features can, for example, be used as indicator for a particular neurological disorder.

Static features can also, depending on the embodiment, serve as indicators. For example, the character topology which simply is the structure of the character in terms of number and manner of pen-stroke can be used, e.g., the existence of alternate forms of a character can indicate a difficulty in the individual to recall specific forms. Character dimension can also be used. For example, various dimensions such as the distance of a character above a writing line, real or extrapolated, the distance of a character below the writing line for those characters requiring line penetration such as 'g', 'p' or 'y,' the area enclosed by loops of letters which comprise loops such as 'a', 'd' or 'o,' and certain deviations from normal can be used above or in some combination(s) as indicators for a given neurological disorder. Another static feature is proportions and ratios, which classify letters based on the ascending, descending and middle zones. Distortions in the proportions and ratios can, for example, be indicative of a given neurological disorder. As can the spacing between characters. Great variations in spacing within and between words can, for example, be an indicator of a given neurological disorder.

Character skew is another static feature that can be used. Character skew is the natural slant of a character. Inconsistent slants can, for example, be an indicator of a given neurological disorder.

Stroke curvature can also be used. Normal handwriting tends to have well rounded curves. A flattening of these curves can, for example, indicate a degradation in handwriting ability.

Another static feature that can be used is simplification. Writers may embellish or ornament writing when confident, but can tend to simplify characters due to diminished ability once a neurological disorder takes hold. The degree of simplification or ornamentation can be used as an indicator by comparison to a known reference.

Character connections can also be used. Most writers connect characters together through one of several conventions; however, a change in the manner of connection or the omission of connections can indicate diminished writing ability due to the onset of a neurological disorder.

Again, techniques, such as those disclosed in related application Ser. No. 10/791,375, can be used for the recognition of certain indicators in handwriting samples. For example, image processing techniques can be used to identify descriptors of the various characters. These descriptors can then be correlated to known letters for recognition purposes. Comparing the same known characters, parts of characters or groups of characters, from different handwriting specimens provides a method for ensuring that the same handwritten features are measured and analyzed for the purpose of detecting change. These same descriptors and techniques can then be used to detect the features described above.

For example, pen pressure can directly be correlated with the thickness of a pen-stroke, because generally, greater pressure leads to a thicker lines. Further, tapers, which can be measured as progressive changes in line thickness, at the beginning and end of words can be correlated to writing speed. The higher frequency of tapers or longer lengths indicate quicker writing speeds. Line continuity can be measured as the number of pen lifts or breaks in strokes found in a writing sample. The more pen lifts, the more discontinuous the writing sample. The steadiness of writing can be measure through the consistency of lines, because tremors can introduce sudden Waves from a line of writing or oscillation. Such deviations can be measured as an indicator of steadiness. The written characters can be disassembled into individual pen-strokes. Isolated random strokes can indicate lack of connectivity. The number and magnitude of these random strokes can be quantified as a measure of connectivity.

Before describing the process for developing and using a diagnostic in more detail, the technology that can be employed will be described briefly. It should be noted that a key to a comparative analysis of handwriting samples is detecting their similarities and differences with precision. Detecting differences and similarities between handwriting samples requires: first, technology that can register or align the samples so that like features can be compared and; second, technology that can measure indiscernible differences between the samples with requisite precision. Related patent application Ser. No. 10/791,375 discloses systems and methods suited to meet both the alignment and the measurement requirements necessary to compare handwriting samples. The same methods that identify individual characters can also be used to extract specification regarding how the character was written, i.e., the character's form, the relationship among its internal features, the sequence of the pen strokes used to create the character and the strength or tentativeness of these strokes. These specifications provide the foundation for handwriting comparisons.

The conceptual basis for the systems and methods described in related application Ser. No. 10/791,375 is Graph Theory and the strength of the technology is in its ability to detect and align similar graphs. For purposes of this discussion, similar graphs are isomorphic graphs that have their features, i.e., edges and vertices, in closely related geometry.

In the case of writing, groups of words, individual words, characters and parts of characters are all represented by lines on paper. These lines assume distinctive shapes representing the letters of the alphabet and numerals. They connect and cross. These lines can be readily transformed into mathematical graphs consisting of edges and vertices connected exactly in the same way as their source pen strokes on paper. Since graphs can be generated from any writing sample, they provide a common denominator among samples. Differences between writing samples can be detected as difference between graphs. The technology disclosed in related application Ser. No. 10/791,375 can be deployed to isolate and detect similar graphs. Once detected, the technology can "register" or align the graph so that corresponding features can be compared directly. Accordingly, words, characters and parts of characters occurring in different words can be isolated and matched. The matching process entails aligning these graphs so that specific features, i.e., edges and vertices, align in such a way that they can be compared.

Some examples of features include the apex of the uppercase "A", the center horizontal line in the uppercase "E" and the loop in the cursive lowercase letter "l". As explained in related application Ser. No. 10/791,375, the graphs become the "caddies" carrying feature information from writing samples in such a way that meaningful comparisons can be made using automated techniques.

Figure 2:
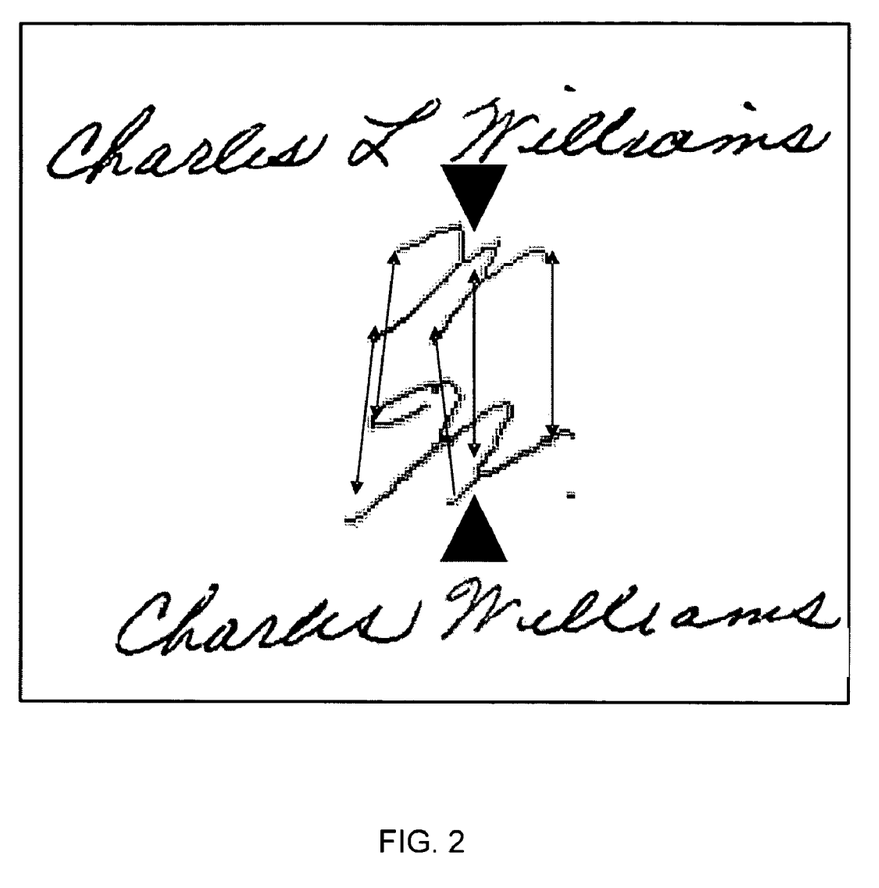
FIG. 2 is a diagram illustrating the concept of handwriting feature alignment through the use of graphs as performed in accordance with one embodiment.

FIG. 2 illustrates the concept of similar feature alignment through the use of graphs. As can be seen, two different samples provide embedded graphs that in turn provide point-to-point registration between similar forms in the two samples. Once similar instances of words, characters and their constituent components such as loops, lines, comers and cusps can be matched and aligned, the technology disclosed in related application Ser. No. 10/791,375 permits detailed comparisons on a feature-to-feature basis. That is, characters from one writing sample can be compared with the same characters from another sample. This comparison can involve numerous component features such as the skew or slant of the component, the shape of the component, the pen pressure in writing a particular stroke, size of characters, the sequence of pen strokes in writing the character, the steadiness or waviness of pen strokes, etc.

These features can then be measured using "Pictographic Agent" technology. The Pictographic Agent can, for example, consist of a suite of software routines that traverse graphs and capture geometric feature data producing results suitable for statistical analysis and interpretation. For instance, a Pictograph agent can be instructed to find all occurrences of a particular letter; extract precise measurements of certain features such as ascending loops, descending loops, connectors, slant, height and width of the character, and the thickness and consistency of the pen strokes; and return this information as numeric data. This numeric data can be provided with great precision, limited only by the resolution of the scanned image. It can then provide the foundation for detailed analyses of the writing samples.

Thus, the technology described can detect the above features statically from latent handwriting samples. This capability provides value in two ways: First, analysis can be performed on historic writing samples such as correspondence or bank checks; and second, the technology does not require any hardware for real time writing capture, enhancing its cost effectiveness as a measurement technique. Real time responses is, however, envisioned. Hence, assuming this technique is used as a diagnostic tool, the results can, for example, be available within thirty minutes of inquiry.

The technology is able to match handwriting features and to quantify the geometric differences between the matched features. This capability overcomes the limitations associated with extracting data from handwriting using conventional techniques, which are very time consuming and laborious, and requires highly skilled technicians usually reviewing writing samples literally "under microscopes".

As mentioned, a key to effective and efficient comparative analysis of handwriting samples is the ability to detect similarities and differences with precision. Detecting differences and similarities requires samples to be registered or aligned with each other so that corresponding handwriting features can be compared. It also requires that differences between the samples can be measured with requisite precision, even those features which may be difficult to discernable on unaided visual inspection of still images such as pen pressure.

Groups of words, individual words, characters and parts of characters are all represented by lines on paper. These lines assume distinctive shapes representing the letters of the alphabet and numerals. They connect and cross. They can also be transformed into mathematical graphs consisting of edges and vertices connected exactly in the same way as their source pen strokes on paper. Since these graphs can be generated from any writing sample, they provide a quantifiable common denominator obtainable from any samples. Differences between writing samples can be detected as differences between graphs. By registering or aligning different graphs, corresponding features of handwriting can be compared directly. Accordingly, word, characters and parts of characters occurring in different words can be isolated and matched.

Change detection in handwriting occurs when differences are measured in individual features drawn from different writing samples collected over time. Generally, as mentioned, features that can be extracted from writing fall into two principal categories: dynamic features and static features. Dynamic features relate to the means and methods of writing and include such factors as pen pressure, line tapers, line continuity, line integrity, and line connectivity. Static features are characteristic of the final written form and encompass topological and geometric information, such as character topology, dimensions, proportions and ratios, spacing, skew, stroke curvature, ornamentation and simplification, and connections. Presumably, others features or more refined variants can be incorporated as required by the condition in question. Each of these features has the potential to be at least a partial indicator for various subject conditions.

A non-exhaustive list of representative dynamic features includes:

(1) Pen pressure. Pen pressure is measured by the variations in the thickness of the pen-stroke in the different writing samples. This is a useful feature to measure, because variations in the pressure consistent with alternating bursts of strength and loss of control may be indicative, for example, of early stage Parkinson's disease.

(2) Tapers. Tapers are used here to mean measurable progressive changes in pen-stroke width. Tapered beginnings and endings of words are indicators of writing speed. Tapers that are either longer or that occur more frequently are indicative of a quicker writing speed (as well as a more confident writer).

(3) Line continuity. The number of pen lifts within words (generally between characters or between the stem and the body of a character) repeated in a given individual's writing sample can be counted and averaged over time. This is useful, because, for example, persons with the onset of neurological disorder may perform pen lifts at an ever increasing rate as the disorder progresses.

(4) Line integrity. Line Integrity measures the steadiness and consistency of lines. These can be examined for tremors in the pen-stroke, especially on long down strokes and in the bodies of characters. For example, tremors can be measured by frequency, degree, and directional variance. They can also be examined by descriptive type, e.g. as a waiver or sudden movement away from and return to the line of writing, or as a rhythmic oscillation (5) Connectivity. This feature entails "disassembling" written characters to discern the sequence in which individual pen-strokes were written. Connectivity detects isolated, random strokes. These strokes, especially when occurring to the left of the commencement of the handwriting, suggesting difficulty in commencing the writing or recalling the constructive sequence for writing characters.

A non-exhaustive list of representative static features includes:

(1) Character topology. Character topology relates to the actual form of the character—its structure in terms of the number of constituent pen-strokes and the manner in which these pen-strokes are arranged. Alternative forms of the same character—called character "allographs"—can also be detected through character topology. This is useful, because topology may indicate the ability of individuals to recall specific memorized forms—or alternative versions of these forms.

(2) Character dimensions. An individual's set of handwriting samples can have different size measurements of each character taken. These measurements can be averaged over a time period for each such character being utilized. For example, measurements can be taken of (1) the average distance above the writing line for each character, with the writing line being extrapolated in unlined papers; (2) the average distance below the line for each character whose form calls for below the line penetration, again with the writing line being extrapolated in unlined papers; or (3) the total area of all interior loops of upper case characters A, D, J, O, Q and lower case a, b, d, g, h, l, m, n, o, p, q, and r (unclosed loops may be extrapolated to closure following the curvature established by the loop at pen lift or along the base line, as appropriate). Examination of this feature is useful, for example, as a significant measure for determination of the onset of micrographia in Parkinson's patients and agraphia in Alzheimer's patients.

(3) Proportions and Ratios. This feature examines the ratios between the various zones within handwriting. Typically, handwriting can be reliably measured in three zones: the descending zone (below the baseline), the middle zone (on the baseline), the ascending zone (extending above the middle zone). This feature is useful for quantifying distortions in character formation resulting from degenerating writing ability.

(4) Spacing. Spacing encompasses the horizontal displacement of characters within words as well as the separation between words. These proportions typically remain consistent in an individual's writing and are well suited for change detection measurement.

(5) Skew. Skew measures the consistent direction of vertical and near vertical slant in a writing sample. Similar to spacing, skew remains consistent across an individual's writing and can be a good measure of change detection.

(6) Stroke Curvature. This feature is measured by the depth of curvature of handwritten elements. Any flattening of curves could suggest degradation of writing capability.

(7) Embellishment or Simplification. Every written character has a basic structural form that is commonly referenced as the "school copy" form of the character. Writers may deviate from this form through the introduction of new elements (ornamentation) or the reduction of elements (simplification). Character simplification may indicate diminishing writing ability.

(8) Character Connections. In cursive writing, there are measurable conventions for joining characters into words. These conventions take four distinct forms called: garlands ("u"), arcades (inverted garland), angles (zigzag), and threads (unstructured). Unlike characters, these connections are not memorized as models but are learned through writing.

Changes in the ways characters are connected or the omission of these connections may indicate underlying degradation in writing ability.

In one embodiment, a handwriting sample is optically scanned into an digital image. The image is then analyzed in terms of mathematical graphs consisting of edges and vertices. Features of a handwriting sample can then be extracted from these graphs to meet both the alignment and the measurement requirements necessary to compare handwriting samples. These features can be measured using software methods that analyzes the image by traversing the graphs and capturing geometric feature data producing results suitable for statistical analysis and interpretation.

For instance, the analysis locates all occurrences of a particular letter; extracts precise measurements of certain features of the letter such as ascending loops, descending loops, connectors, slant, height and width of the character, and the thickness and consistency of the pen strokes; and returns this information as quantitative numeric data. The numeric data should be provided with great precision, limited only by the resolution of the scanned image. The resulting data provides the foundation for detailed analyses of the writing samples. For example, image processing techniques can be used to identify descriptors of the various characters. These descriptors can then be correlated to known letters for recognition purposes. Comparing the same known characters, parts of characters or groups of characters, from different handwriting specimens provides a method for ensuring that the same handwritten features are measured and analyzed for the purpose of detecting change. These same descriptors and techniques can then be used to detect the features described previously.

Using dynamic and static features from fixed images, i.e. from latent handwriting samples already in existence is valuable in at least two ways: to enable analysis on historic writing samples such as correspondence or bank checks; to be free from the requirement of having specialized hardware for real-time writing capture. Real-time responses is, however, would also be valuable to enable rapid results of an inquiry, if, for example, the technique is used in a clinical setting requiring rapid assessment.

Once similar instances of words, characters and their constituent components are isolated, matched, and aligned, detailed comparisons on a feature-to-feature basis between different samples can be made.

Changes in handwriting can be correlated with the onset or progression of certain disorders affecting fine motor skills. For example, the alternating burst of strength and loss of control in early stage Parkinson's disease can manifest itself in pen pressure inconsistency. Similarly, the speed of writing can be indicative of writing confidence, which would be lower in a subject with a neurological disorder. Other examples include the increasing breakdown of line continuity within words and between, the deterioration of the steadiness of writing, or changes in the connectivity of character. For example, the existence and number of disconnected isolated random stroke can indicate difficulty commencing writing or recalling the constructive sequence for writing. Depending on the embodiment, all or some of features like those described previously can, for example, be used as indicators for a particular target disorder.

In order to maximize both the extent and the level of confidence of the analysis in identifying relevant features, the collection. of handwriting samples from each participant has certain ideal characteristics. For instance, more valuable information is obtained if the collection extends back to that point in time where the variations noted in the handwriting have not yet appeared (e.g. stabilized along the horizontal axis); contains more than five separate writing samples of more than one hundred words each for each time period analyzed; consists of handwriting samples occurring in the normal course of that participants daily activities (as distinguished from samples given a part of a research process); consists of samples repetitive words and phrases, with the same wording for the same normal function; and is from participants where the frequency of writing is generally unaltered or uninterrupted over the time period analyzed.

For example, a potentially useful source of handwriting samples is an individual's cancelled checks, either from the bank's cancelled check image archive for that individual or copies of cancelled checks that person has saved. Alternatively, a collection of handwritten paperwork can be used. Since target disorders are often progressive, features should be analyzed in the course of handwriting samples taken over a long period, such as a period of years. By noting trends in the changes in certain features of handwriting samples over a long period, early detection of the onset of certain target disorders can be achieved. A high degree of precision is required, and a plurality of features should be tracked to accurately analyze handwriting for these indicators. In addition, a large number of handwriting samples can be used to further increase accuracy.

An analytical process to evaluate handwriting as a marker for certain target disorders can now be described. The process involves comparing the changes in handwriting over time from a group of persons free of one of the targets disorders, simply experiencing the normal aging process ("baseline group"), to the changes in handwriting over time from a group of persons known to have developed a specific target disorder ("sample group"). Composition of the sample group consist of patients having, for example, dementia of the Alzheimer's type, Parkinson's disease (with and without dementia), frontotemporal dementia, dementia with Lewy bodies, or Huntington's disease. For any given condition, the analytical process requires identifying the set of handwriting features which are attributable to that condition.

Figure 3:
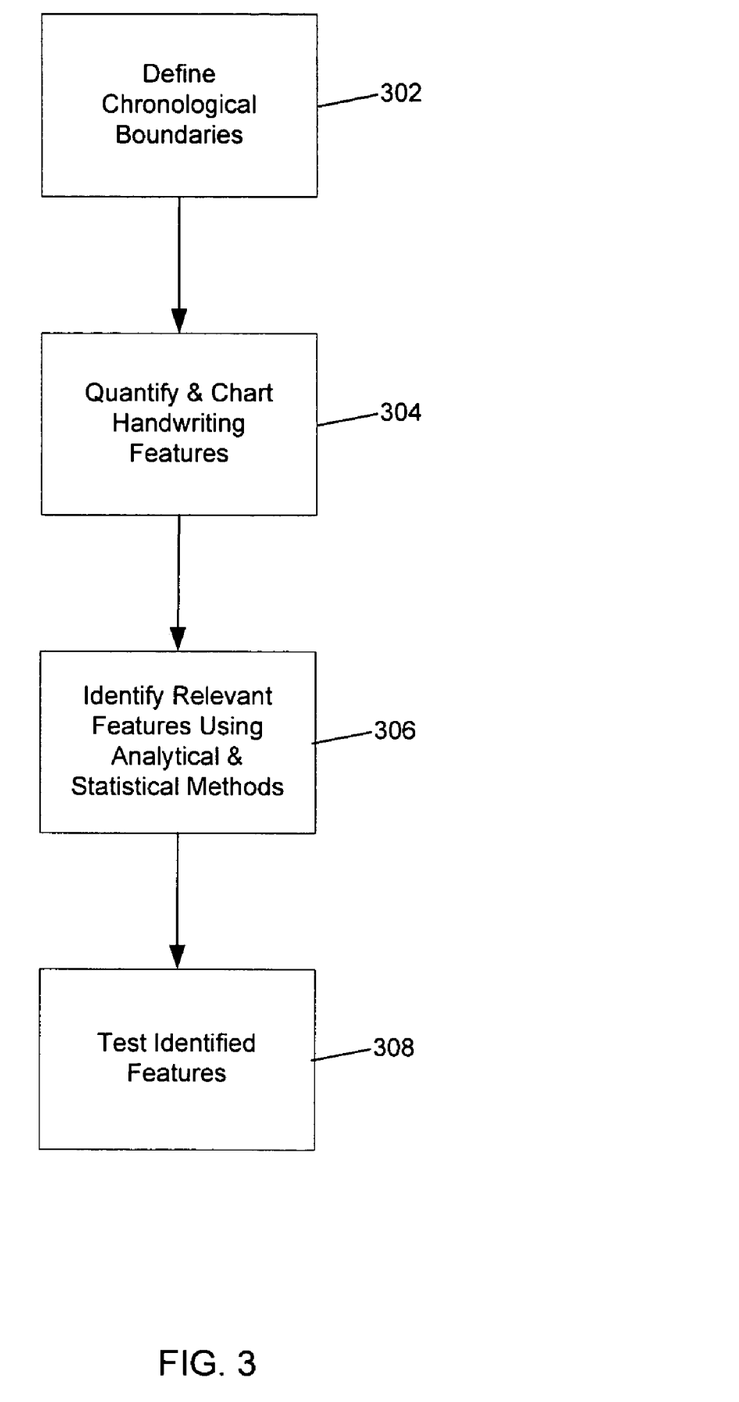
FIG. 3 is a flow chart illustrating and example process for identifying handwriting features indicative of a disorder affecting fine motor skills.

Historical handwriting samples and contemporary handwriting samples from both groups are used to extract a set of features that can be reliably measured and tracked over time. The process of identification of this feature set involves four steps, as illustrated in FIG. 3.

First, in step 302, chronological boundaries are established for each participant, regardless of the group, for each feature deviation that is the subject of analysis. For instance, the stop date may be the date of the last testing, so that the analysis can be extended into the future as appropriate. While start date may be the horizontal axis, being that time period immediately preceding commencement of the specific feature being analyzed.

Next, in step 304, for each individual in a group, handwriting samples over a fixed time period are analyzed together and the features of that sample are quantified and charted. The values of the features being the average over all available samples (with appropriate treatment of extremes variants to protect against anomalies). For example, with the feature related to size of characters, the baseline is the size of characters at the start date (the horizontal axis), with all subsequently fixed time periods being charted based upon the average of all examples during that period in accordance with consistently quantified variations from this start point.

In step 306, and in conjunction with an expert in the disorder being studies, e.g. a neurologist, further analytical and statistical analysis is undertaken in order to determine those relevant features which can be used to develop diagnostic tools.

In step 308, the diagnostic tools are tested by challenging the identified features against new patients to determine the accuracy of the tools when deployed.

The end product of the process is a diagnostic tool consisting of knowledge of which features are attributable to a given condition, how those features may change with time or progression of that condition, and how to correlate that knowledge with a new sample collections from new individuals to detect or monitor the progression of the underlying condition.

While certain embodiments of the inventions have been described above, it will be understood that the embodiments described are by way of example only. Accordingly, the inventions should not be limited based on the described embodiments. Rather, the scope of the inventions described herein should only be limited in light of the claims that follow when taken in conjunction with the above description and accompanying drawings.

What is claimed:

1. In an image recognition system comprising an image graph constructor and a comparison module, a method for detecting target disorders, comprising:
   optically scanning a plurality of writing samples for each of a plurality of known subjects;
   storing the optically scanned writing samples in a database;
   grouping the samples chronologically;
   analyzing the optical scanned writing samples to detect trends, wherein analyzing the optical scanned writing samples includes:
      converting the optical scanned writing samples into a plurality of image graphs comprising edges and vertices using the image graph constructor,
      traversing each of the plurality of image graphs to capture data related to various geometric features included in the graphs, and
      comparing the data related to the various geometric features for the plurality of image graphs using the comparison module and assigning a value to each geometric feature for each of the plurality of image graphs, the assigned values being used to determine whether a trend in the writing samples associated with a given target disorder can be discerned.

2. The method of claim 1, wherein the geometric features include dynamic features.

3. The method of claim 2, wherein the dynamic features include pen pressure.

4. The method of claim 2, wherein the dynamic features include tapers.

5. The method of claim 2, wherein the dynamic features include line continuity.

6. The method of claim 2, wherein the dynamic features include line integrity.

7. The method of claim 2, wherein the dynamic features include connectivity.

8. The method of claim 1, wherein the geometric features include static features.

9. The method of claim 8, wherein the static features include character topology.

10. The method of claim 8, wherein the static features include character dimensions.

11. The method of claim 8, wherein the static features include proportions and ratios.

12. The method of claim 8, wherein the static features include spacing.

13. The method of claim 8, wherein the static features include skew.

14. The method of claim 8, wherein the static features include embellishments or simplifications.

15. The method of claim 8, wherein the static features include character connections.

16. The method of claim 1, wherein grouping the writing samples chronologically comprises defining a plurality of time periods and grouping the plurality of writing samples by time period based on when the writing sample was created, and wherein the method further comprises averaging the values for each geometric feature for the plurality of image graphs for each time period and for each of the plurality of known subjects.

17. The method of claim 16, wherein determining whether a trend in the writing samples associated with a given target disorder can be discerned comprises determining whether at least one of the values or average values associated with certain geometric features associated with the known subjects that exhibit the target disorder exhibit an identifiable trend that can be reliably associated with the target disorder.

18. the method of claim 17, wherein determining whether at least one of the values or average values exhibit an identifiable trend that can be reliably associated with the target disorder comprises comparing at least one of the values and average values of the geometric features of the associate image graphs associated with the known subjects that exhibit the target disorder with the values and average values of the image graphs associated with known subjects that do not exhibit the target disorder.

19. An image recognition system having a processor for detecting target disorders, comprising:
   a database configured to store a plurality of optically scanned writing samples that are grouped chronologically;
   an image graph constructor coupled with the database, the image graph constructor configured to convert the optical scanned writing samples into a plurality of image graphs comprising edges and vertices;
   an agent configured to traverse each of the plurality of image graphs to capture data related to various geometric features included in the image graphs, and
   a comparison module configured to compare the data related to the various geometric features for the plurality of image graphs to determine whether a trend in the writing samples associated with a given target disorder can be discerned.

20. The image recognition system of claim 19, wherein the comparison module is further configured, for each of the plurality of users, to compare the data related to the various geometric features for image graphs of one chronological time period to those of a previous time period.

21. The image recognition system of claim 20, wherein the comparison module is further configured to match isolated constituent components in the image graphs.

22. The image recognition system of claim 21, wherein the comparison module is further configured to align constituent components in the matched image graphs.

23. The image recognition system of claim 22, wherein the comparison module is further configured to perform detailed comparisons on a feature by feature basis between the aligned image graphs.

24. The image recognition system of claim 19, wherein the comparison module is further configured to assign a value to each geometric feature for each of the plurality of image graphs, the assigned values being used to determine whether a trend in the writing samples associated with a given target disorder can be discerned.

25. The image recognition system of claim 24, wherein grouping the writing samples chronologically comprises defining a plurality of time periods and grouping the plurality of writing samples by time period based on when the writing sample was created, and the comparison module is further configured to average the values for each geometric feature for the plurality of image graphs for each time period and for each of the plurality of known subjects.

26. The image recognition system of claim 25, wherein determining whether a trend in the writing samples associated with a given target disorder can be discerned comprises determining whether at least one of the values or average values associated with certain geometric features associated with the known subjects that exhibit the target disorder exhibit an identifiable trend that can be reliably associated with the target disorder.

27. the image recognition system of claim 26, wherein determining whether at least one of the values or average values exhibit an identifiable trend that can be reliably associated with the target disorder comprises comparing at least one of the values and average values of the geometric features of the associate image graphs associated with the known subjects that exhibit the target disorder with the values and average values of the image graphs associated with known subjects that do not exhibit the target disorder.

28. an image recognition system having a processor comprising an image graph constructor and a comparison module, the system detecting target disorders, comprising:
   optically scanning a plurality of writing samples for each of a plurality of known subjects;
   storing the optically scanned writing samples in a database;
   grouping the samples chronologically;
   for each of the plurality of known subjects, analyzing the optical scanned writing samples to detect trends, wherein analyzing the optical scanned writing samples includes:
      converting the optical scanned writing samples into a plurality of image graphs comprising edges and vertices using the image graph constructor,
      traversing each of the plurality of image graphs to capture data related to various geometric features included in the graphs, and
      comparing the data related to the various geometric features for image graphs of one chronological time period to those of a previous time period using the comparison module to determine whether a trend in the writing samples associated with a given target disorder can be discerned.

29. The system of claim 28, wherein comparing the data related to the various geometric features for the plurality of image graphs comprises matching isolated constituent components in the image graphs.

30. The system of claim 29, wherein comparing the data related to the various geometric features for the plurality of image graphs further comprises aligning constituent components in the matched image graphs.

31. The system of claim 28, wherein the geometric features include dynamic features.

32. The system of claim 31, wherein the dynamic features include pen pressure.

33. The system of claim 31, wherein the dynamic features include tapers.

34. The system of claim 31, wherein the dynamic features include line continuity.

35. The system of claim 31, wherein the dynamic features include line integrity.

36. The system of claim 31, wherein the dynamic features include connectivity.

37. The system of claim 28, wherein the geometric features include static features.

38. The system of claim 37, wherein the static features include character topology.

39. The system of claim 37, wherein the static features include character dimensions.

40. The system of claim 37, wherein the static features include proportions and ratios.

41. The system of claim 37, wherein the static features include spacing.

42. The system of claim 37, wherein the static features include skew.

43. The system of claim 37, wherein the static features include embellishments or simplifications.

44. The system of claim 37, wherein the static features include character connections.

* * * * *

UNITED STATES PATENT AND TRADEMARK OFFICE
CERTIFICATE OF CORRECTION

PATENT NO.      : 7,636,457 B2                                       Page 1 of 1
APPLICATION NO. : 10/896642
DATED           : December 22, 2009
INVENTOR(S)     : Franke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1464 days.

Signed and Sealed this

Ninth Day of November, 2010

David J. Kappos
*Director of the United States Patent and Trademark Office*